United States Patent [19]

Zizek

[11] Patent Number: 4,855,439
[45] Date of Patent: Aug. 8, 1989

[54] PROCESS FOR THE PREPARATION OF CIMETIDINE

[75] Inventor: Teofil Zizek, Ljubljana, Yugoslavia

[73] Assignee: LEK, Ljubljana, Yugoslavia

[21] Appl. No.: 147,423

[22] Filed: Jan. 25, 1988

[30] Foreign Application Priority Data

Jan. 23, 1987 [YU] Yugoslavia .............................. 91/87

[51] Int. Cl.$^4$ ........................................... C07D 233/64
[52] U.S. Cl. .................................................... 548/342
[58] Field of Search ......................................... 548/342

[56] References Cited

U.S. PATENT DOCUMENTS 4,720,552  1/1988  Zizek et al. ......................... 548/342

FOREIGN PATENT DOCUMENTS 2855836  7/1979  Fed. Rep. of Germany .

OTHER PUBLICATIONS

Yanko, Chemical Abstracts, vol. 106, Entry 137953q (1987).

J. B. Hendrickson et al., Organic Chemistry, (1970), 410.

D. Barton, Comprehensive Organic Chemistry, vol. 3, (1979), 3–13.

R. B. Wagner et al., Synthetic Organic Chemistry, (1953), 787.

*Primary Examiner*—John M. Ford
*Attorney, Agent, or Firm*—Pollock, Vande Sande & Priddy

[57] ABSTRACT

A new and simple process for the preparation of crystalline cimetidine (N-cyano-N'-methyl-N''-{2/(5-methyl-1H-imidazole-4-yl)methylthio/ethyl}guanidine) is described, wherein cimetidine is obtained by reacting O-ethyl-S-(4-methylimidazolyl-5-methyl)dithiocarbonate hydrobromide with N-cyano-N'-methyl-N''-(2-chloroethyl)guanidine in an aqueous methylamine solution at a temperature between room temperature and the reflux temperature of the reaction mixture, whereupon the desired compound is separated.

Cimetidine is a valuable drug in the therapy of the ulcer disease.

4 Claims, No Drawings

PROCESS FOR THE PREPARATION OF CIMETIDINE

TECHNICAL FIELD OF THE INVENTION (IPC C 07 D 233/64)

The present invention relates to a new process for the preparation of crystalline cimetidine, i.e. N-cyano-N'-methyl-N''-{2/(5-methyl-1H-imidazole-4-yl)methylthio/ethyl}guanidine of the formula

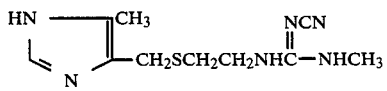

Cimetidine is an exceptionally efficient antagonist of histamine on $H_2$ receptors. It has a hindering effect upon the secretion of gastric acid and for this reason it is used in the therapy of the ulcer disease.

TECHNICAL PROBLEM

There exists a constant need for a technologically advantageous new process for the preparation of crystalline cimetidine, which would provide the desired compound in an excellent yield, with high purity and in a form that can be easily isolated from the reaction mixture.

Prior Art

Cimetidine (N-cyano-N'-methyl-N''-}2/(5-methyl-1H-imidazole-4-yl)methylthio/ethyl}guanidine) is a known compound, which was disclosed for the first time in GB Pat. No. 1,338,169. In GB patent of addition No. 1,397,436 to the former GB patent, there are also disclosed processes for the preparation of cimetidine. These processes, which are schematically shown on page 3, are based on the reaction of 4-halomethyl-, 4-hydroxymethyl- or 4-methoxymethyl-5-methylimidazole and its hydrohalogenide, respectively, with cysteamine hydrochloride (in this scheme X in formula I stands for a halo, a hydroxy or a methoxy group).

The reaction results in the formation of the intermediate compound 4-/(2-aminoethyl)-thiomethyl/-5-methyl-imidazole and its dihydrohalogenide, respectively, which is reacted with methyl isothiocyanate to form N-methyl-N'-}2/(4-imidazolyl-5-methyl)methylthio/ethyl}thiourea, which is then reacted with lead cyanamide to yield cimetidine.

Cimetidine can also be obtained by reacting 4-/(2-aminoethyl)thiomethyl/-5-methyl-imidazole with N-cyano-N',S-dimethylisothiourea or with dimethylcyanodithioimido carbonate to form N-cyano-N'-{2-/(5-methylimidazole-4-yl)methylthio/ethyl}-S-methylisothiourea, which is reacted with methylamine to yield the desired compound. Among these processes the last one provides the best results, the overall yield of the reaction being up to 60%.

There are described several more processes for the preparation of cimetidine in the patent literature. In DE Offenlegungsschrift No. 28 55 836 there is described a process which is based on the reaction of 4-methyl-5-mercaptomethyl imidazole with 1-(N-methyl-N'-cyanocarboxamidino)-aziridine and on the reaction of 4-methyl-5-mercaptomethyl imidazole (in the form of sodium mercaptide) with N-(2-bromoethyl)-N'-methyl-N''-cyanoguanidine, respectively, in an ethanolic solution.

The starting 4-methyl-5-mercaptomethyl imidazole is prepared in a known manner, which is described in the literature for the synthesis of thiols by converting 4-ethoxy-diethioformyl-2,3-diketo-butane to 4-methyl-5-(ethoxy-dithioformyl)imidazole, which is then hydrolyzed with HCl at the reflux temperature of the reaction mixture under a nitrogen atmosphere to give 4-methyl-5-mercaptomethyl imidazole hydrochloride in a yield of 70% (Examples 1–3 of the above DE Offenlegungsschrift). In Example 6 of the same application a variant of this process is described, wherein 4-methyl-5-chloromethyl imidazole is reacted with potassium ethylxanthate in an ethanolic solution at the reflux temperature of the reaction mixture to form 4-methyl-5-(ethoxy-dithioformyl)imidazole, which is

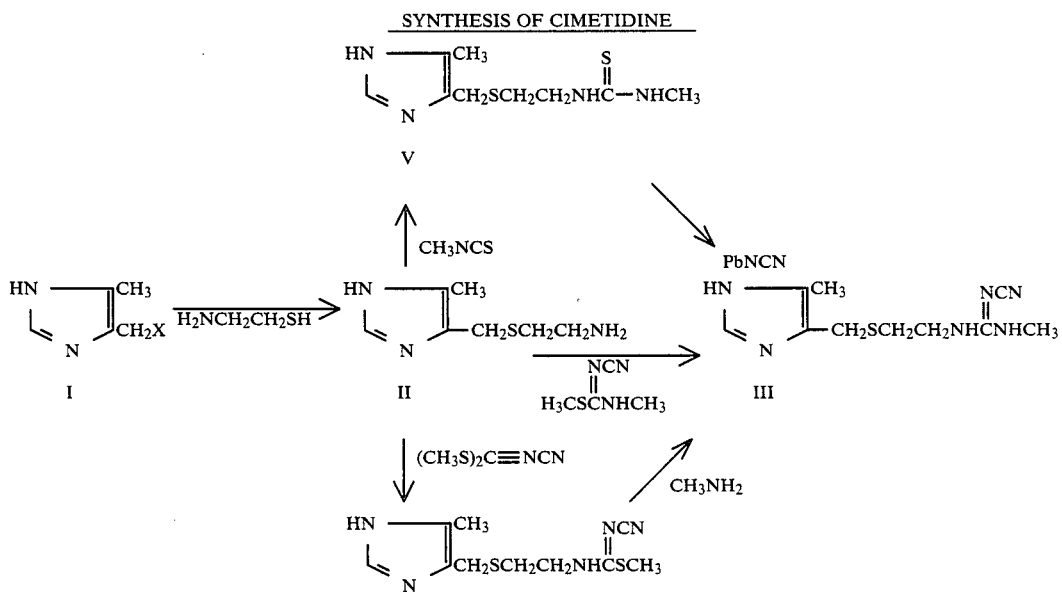

SYNTHESIS OF CIMETIDINE then hydrolyzed as described above to yield 4-methyl-5-mercaptomethyl imidazole hydrochloride.

A drawback of said process is the preparation of the starting 1-(N-methyl-N'-cyanocarboxamido)aziridine using the hazardous, very toxic and even carcinogenic aziridine (ethyleneimine).

In the second variant the results are unsatisfactory due to the instability of N-(2-bromoethyl)-N'-methyl-N''-cyanoguanidine.

A further process, described in the CA Reissue No. 1,209,153 of the patent No. 1,121,363, is based on the reaction of 5-methyl-4-thiomethyl imidazole (in the form of its hydrochloride salt) with N-cyano-N'-methyl-N''-(2-chloroethyl)guanidine. The process provides the desired compound in a high yield, avoiding at the same time the use of the disadvantageous reactants, which are used in the DE Offenlegungsschrift No. 28 55 836.

SUMMARY OF INVENTION

The object of the invention is the preparation of crystalline cimetidine in a new, simple manner by the reaction of O-ethyl-S-(4-methyl-imidazolyl-5-methyl)dithiocarbonate (in the form of its hydrobromide salt) with N-cyano-N'-methyl-N''-(2-chloroethyl)guanidine in an excellent yield, with high purity and a simple isolation from the reaction mixture. This object is achieved by reacting the above two compounds at a temperature between room temperature and the reflux temperature of the reaction mixture in an aqueous methylamine solution, which maintains the basicity of the medium.

Both above compounds are known from the above-mentioned literature.

BEST AND VARIOUS MODES FOR CARRYING OUT INVENTION

O-ethyl-S-(4-methyl-imidazolyl-5-methyl)dithiocarbonate (in the form of its hydrobromide) of the formula

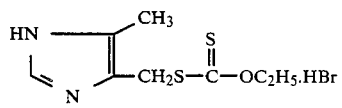

was prepared according to the process described in U.S. Pat. No. 4,270,552. 4(5)-methyl-5(4)-bromomethyl imidazole hydrobromide, which is a known compound described in literature (H. G. Lennartz, W. Schunack, Arch. Pharm. (Weinhein) 310, 1019–1022, 1977; P. Kairisalo, E. Honkanen, Arch. Pharm. (Weinhein) 316, 688–690, 1983; R. Tozo et al, Gazz. Chim. Ital 109, 529–533, 1979), is reacted with potassium O-ethyl dithiocarbonate in an aqueous medium at room temperature to the intermediate O-ethyl-S-(4-methyl-imidazolyl-5-methyl)dithiocarbonate, which is, without isolation, immediately hydrolyzed in the presence of a diluted aqueous solution of HBr or HCl to 4(5)-methyl-5(4)-thiomethyl imidazole in the form of its hydrobromide or hydrochloride salt. The yield of the synthesis is 85%.

The reaction is carried out in nitrogen atmosphere in order to prevent the formation of disulfide as a result of the oxidation of the desired thiol. It was found that, contrary to the processed described in DE Offenlegungsschrift No. 28 55 836, there is no need to hydrolyze this compound in an acidic medium to 4-methyl-5-mercaptoethyl-imidazole; instead, it can be reacted with N-cyano-N'-methyl-N''-(2-chloroethyl)guanidine in the presence of an aqueous methylamine solution at a temperature between room temperature and the reflux temperature of the reaction mixture directly to cimetidine.

In the overall synthesis of cimetidine, this represents the omission of one step, thus simplifying and cheapening the process. Moreover, some expensive solvents, which are used in the above-mentioned prior art processes, are no longer necessary. A further advantage is a simple isolation of crystalline cimetidine in a pure form.

The second reactant, i.e. N-cyano-N'-methyl-N''-(2-chloroethyl)guanidine, is advantageously prepared in the manner described in the YU patent application P No. 2151/83 and in the article by J. Žmitek et al., Org. Prep. Proced. Int. Vol. 17, No. 4–5 (1985) 256–261 N-cyano-N'-methyl-N''-(2-chloroethyl)-guanidine, can be prepared by using dimethyl-(N-cyano-imido)-carbonate of the formula

as the starting material.

Dimethyl-(N-cyanoimido)carbonate is a known compound. Its preparation was described e.g. in J. Org. Chem. 1974, 39, 1522. According to the process of Yugoslavian Application No. P-2151/83, dimethyl-(N-cyanoimido)carbonate is reacted with chloroethylamine hydrochloride hydrobromide to N-cyano-N'-(2-chloroethyl)-O-methyl-isourea, which is reacted with methylamine to yield the N-cyano-N'-methyl-N''-(2-chloroethyl)guanidine.

For a successful course of the reaction the succession of the addition of reactants is important since 4(5)-methyl-5(4)-thiomethyl imidazole is formed in situ and immediately reacted with N-cyano-N'-methyl-N''-(2-chloroethyl)guanidine to yield cimetidine.

The invention is illustrated by the following non-limiting Example.

EXAMPLE

N-cyano-N'-methyl-N''-{2/(5-methyl-1H-imidazole-4-yl)methylthio/ethyl}guandine

N-cyano-N'-methyl-N''-(2-chloroethyl)guanidine (16.0 g, 0.1 mole) is suspended in aqueous 40% methylamine (150 ml). O-ethyl-S-(4-methyl-imidazolyl-5-methyl)dithiocarbonate hydrobromide (29.7 g, 0.1 mole) is added thereto and the reaction mixture is heated for 30 minutes to the reflux temperature. Then the reaction mixture is slowly cooled and stirred at room temperature for 4 hours. White crystals, which separate, are sucked off and washed with water. Thus, there are obtained 17.6 g (70%) of the desired compound, m.p. 140° to 142° C.

I claim:

1. A process for the preparation of crystalline cimetidine (N-cyano-N'-methyl-N''-{2/(5-methyl-1H-imidazole-4-yl)methylthio/ethyl}guanidine) of the formula

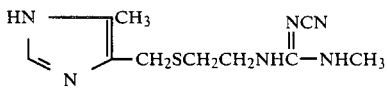

characterized in that O-ethyl-S-(4-methyl-imidazolyl-5-methyl)dithiocarbonate hydrobromide is reacted with N-cyano-N'-methyl-N''-(2-chloroethyl)guanidine in an aqueous methylamine solution at a temperature between room temperature and the reflux temperature of the reaction mixture, whereupon this title compound is separated.

2. The process of claim 1 wherein said methylamine solution is a 40% aqueous solution.

3. The process of claim 1 wherein said temperature is the reflux temperature of the reaction mixture.

4. The process of claim 1 wherein the reaction mixture is cooled to room temperature to thereby separate the desired product from the reaction mixture.

* * * * *